US008119782B2

(12) United States Patent  
MacDonald et al.

(10) Patent No.: US 8,119,782 B2  
(45) Date of Patent: Feb. 21, 2012

(54) MEDIUM SCALE INTEGRATION OF MOLECULAR LOGIC GATES IN AN AUTOMATON

(75) Inventors: Joanne MacDonald, New York, NY (US); Milan N. Stojanovic, Fort Lee, NJ (US); Darko Stefanovic, Albuquerque, NM (US)

(73) Assignee: The Trustees of Columbia University in the City of New York, New York, NY (US)

( * ) Notice: Subject to any disclaimer, the term of this patent is extended or adjusted under 35 U.S.C. 154(b) by 453 days.

(21) Appl. No.: 12/319,835

(22) Filed: Jan. 12, 2009

(65) Prior Publication Data

US 2009/0275027 A1    Nov. 5, 2009

Related U.S. Application Data

(63) Continuation of application No. 11/904,667, filed on Sep. 28, 2007, now abandoned.

(60) Provisional application No. 60/847,873, filed on Sep. 28, 2006.

(51) Int. Cl.  
*C07H 21/04* (2006.01)

(52) U.S. Cl. .................................... 536/23.1

(58) Field of Classification Search ........................ None  
See application file for complete search history.

(56) References Cited

OTHER PUBLICATIONS

Adleman, L. M. Science 1994, 266, 1021-4.  
Elowitz, M. B.; Leibler, S. Nature 2000. 403, 335-8.  
Mao, C; LaBean, T. H.; Relf, J. H.; Seeman, N. C. Nature 2000, 407, 493-6.  
Benenson. Y.; Paz-Elizur, T.; Adar, R.; Keinan, E.; Livnch, Z.; Shapiro, E. Nature 2001. 414, 430-4.  
Braich, R. S.; Chelyapov, N.; Johnson, C; Rothemund, P. W.; Adleman, L. Science 2002, 296, 499-502.  
Stojanovic, M. N.; Mitchell, T. E.; Stefanovic, D. J. Am. Chern. Soc. 2002, 124. 3555-61.  
Stojanovic, M. N.; Stefanovic, D. J. Am. Chem. Soc. 2003, 125, 6673-6.  
Stojanovic, M. N.; Stefanovic, D. Nat. Biotechnol. 2003, 21, 1069-74.  
Adar, R.; Benenson, Y.; Linshiz, G.; Rosner, A.; Tishby, N.; Shapiro, E. Proc. Natl. Acad. Sci. U.S.A. 2004, 101, 9960-5.  
Benenson, Y.; Gil, B.; Ben-Dor, U.; Adar, R.; Shapiro, E. Nature 2004, 429, 423-9.  
De Silva. A. P.; McClenaghan, N. D. Chemistry 2004, 10, 574-86.  
Rothemund, P. W.; Papadakis, N.; Winfree, E., PLoS Biol. 2004, 2. c424.  
Schmidt, K. A.; Henkel, C. V.; Rozenberg, G.; Spaink. H. P. Nucleic Acids Res. 2004, 32, 4962-8.  
Simpson, M. L. Trends Biotechnol. 2004, 22, 555-7.  
Su, X.; Smith, L. M. Nucleic Acids Res. 2004, 32, 3115-23.  
Szacilowski, K. Chemistry 2004, 10, 2520-8.

(Continued)

*Primary Examiner* — Samuel Woolwine  
(74) *Attorney, Agent, or Firm* — John P. White; Cooper & Dunham LLP

(57) ABSTRACT

The development of the first solution-phase molecular assembly comprising over 100 molecular logic gates, which more than quadruples the complexity performed by any previous system. "MAYA-II" is a second generation molecular automaton capable of playing a complete game of tic-tac-toe against a human opponent, and encompasses 76 permissible game plays. MAYA-II is more user-friendly than MAYA-I, as it signals both players move in a two-color output system and imposes no constraints on the position of the human player's first move. MAYA-II is constructed from three classes of stem-loop controlled deoxyribozyme-based logic gates that are allosterically modulated by input oligonucleotides to produce fluorescent output signals.

21 Claims, 3 Drawing Sheets

OTHER PUBLICATIONS

Benner, S. A.; Sismour, A. M. Nat. Rev. Genet. 2005, 6. 533-43.

Grover, W H , Mathies, R A. Lab Chip 2005, 5:1033-40.

Stojanovic, M N, Semova, S, Kolpashchikov, D, Macdonald, J, Morgan, C, Stefanovic, D, J. Am. Chem. Soc. 2005, 127, 6914-5.

de Silva, A P, Leydet, Y, Lmcheneau. C, McClenaghan, ND, J. Phys. Condens. Matter 2006, 18:S1847-72.

Henkel, C V, Back, T, Kok, J N, Rozenberg, G, Spaink, H P Biosvstems, 2006.

Isaacs, F J , Dwyer, D J , Collins, J J Nat Biotethnol 2006, 24, 545-54.

Komiya. K, Sakamoto, K, Kameda, A, Yamamoto, M, Ohuchi, A, Kiga, D, Yokoyama, S, Hagiya, M, Biosystems 2006. 83:18-25.

Lederman, H, Macdonald, J, Stefanovic, D, Stojanovic, M N, Biochemistry 2006, 45, 1194-99.

Liu, Y, Jiang, W, Zhang, H Y, Li, C J, J. Phys. Chem. B 2006, 110, 14231-35.

Magri, D C, Brown, G J, McClean, GD, de Silva, A P, J. Am. Chem. Soc. 2006, 725,4950-1.

Penchovsky, R, Breaker, R R, Nat. Biotechnol. 2005, 23, 1424-33.

Andrews, B, Games, Strategies, and Boolean Formula Manipulation In Dept of Computer Science Uni. of New Mexico UNM CS Tech Rep TR-CS-2005-41, University of New Mexico, 2005.

Mauri, G, Ferretti, C, In Word design for molecular computing: A survey, 9th International Workshop on DNA-Based Computers, 2003, Springer, 2004. pp. 37-46.

Sager, J, Stefanovic, D, In Designing Nucleotide Sequences for Computation: A Survey of Constraints, 11th International Workshop on DNA-Based Computers,. 2005, Springer, 2006, pp. 275-289.

Seeman, N C, J. Theor. Biol. 1982, 99:237-47.

Zuker, M, Nucleic Acids Res. 2003, 31, 3406-15.

Breaker. R R, Joyce, G F, Chem. Biol. 1995, 2, 655-60.

Santoro. S W, Joyce, G F, Proc. Natl. Acad. Sci. USA 1997, 94:4262-6.

Macdonald, J, Stefanovic, D, Stojanovic, M N, Solution-Phase Moleculai-Scale Computation With Deoxyribozyme-Based Logic Gates and Fluorescent Readouts In Fluorescent energy transfer nucleic acid probes designs and protocols, Didenko, V V, Ed., Humana Press Inc., Totowa, NJ, 2006, vol. 335, pp. 343-363.

Wright. M C, Joyce, G F Science 1997, 276, 614-617.

Kolpashchikov, D M, Stojanovic, M N, J. Am. Chem. Soc. 2005, 127, 11348-51.

SEQUENCE LISTING

```
<160> NUMBER OF SEQ ID NOS: 44

<210> SEQ ID NO 1
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 1
```
aacgactgca ccacg                                        15

<210> SEQ ID NO 2
<211> LENGTH: 15
<212> TYPE: DNA
<213> ORGANISM: ARTIFICIAL SEQUENCE
<220> FEATURE:
<223> OTHER INFORMATION: CHEMICALLY SNYTHESIZED SEQUENCE

<400> SEQUENCE: 2
ctctccctgt accca                                        15

<210> SEQ ID NO 3
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 3
acccctctcg ctctt                                        15

<210> SEQ ID NO 4
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 4
ttctgccttg atccg                                        15

<210> SEQ ID NO 5
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 5
tgttgtctta tccat                                        15

<210> SEQ ID NO 6
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 6
tcagatgcta cgtgt                                        15

<210> SEQ ID NO 7
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 7
accgtactcg accta                                        15

<210> SEQ ID NO 8
<211> LENGTH: 15
<212> TYPE: DNA
<213> ORGANISM: ARTIFICIAL SEQUENCE
<220> FEATURE:

<223> OTHER INFORMATION: CHEMICALLY SYNTHESIZED SEQUENCE

<400> SEQUENCE: 8
tcggatctcg gtttc                                                        15

<210> SEQ ID NO 9
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 9
tacacgctgg tcaat                                                        15

<210> SEQ ID NO 10
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 10
cactatctcg aatca                                                        15

<210> SEQ ID NO 11
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 11
gcgtgactgc ggcat                                                        15

<210> SEQ ID NO 12
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 12
gttggtcttg tagga                                                        15

<210> SEQ ID NO 13
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 13
gctaggctat cgcgt                                                        15

<210> SEQ ID NO 14
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 14
taatacctga gcggg                                                        15

<210> SEQ ID NO 15

```
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 15
taccccctag tctgc                                                      15

<210> SEQ ID NO 16
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 16
aacggacttc aacag                                                      15

<210> SEQ ID NO 17
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 17
cgggatctcg tcggt                                                      15

<210> SEQ ID NO 18
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 18
atcgctctcc atgca                                                      15

<210> SEQ ID NO 19
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 19
atctatctcg ttccg                                                      15

<210> SEQ ID NO 20
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 20
actccgctcg actta                                                      15

<210> SEQ ID NO 21
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 21
```
ggatcactta cgtat                                                    15

<210> SEQ ID NO 22
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 22
ggtagccttt tatcg                                                    15

<210> SEQ ID NO 23
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 23
cattgcctcg atatc                                                    15

<210> SEQ ID NO 24
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 24
ccagaccttt caagt                                                    15

<210> SEQ ID NO 25
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 25
tgcgtacttt gggtc                                                    15

<210> SEQ ID NO 26
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 26
tcagggctac gcaag                                                    15

<210> SEQ ID NO 27
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 27
taattactgt ttcac                                                    15

<210> SEQ ID NO 28
<211> LENGTH: 15
<212> TYPE: DNA
<213> ORGANISM: ARTIFICIAL SEQUENCE
<220> FEATURE:

```
<223> OTHER INFORMATION: CHEMICALLY SYNTHESIZED SEQUENCE

<400> SEQUENCE: 28
ggatgcctgg cgtct                                                         15

<210> SEQ ID NO 29
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 29
tgctatctcg acaag                                                         15

<210> SEQ ID NO 30
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 30
ctcaggctgt gtatt                                                         15

<210> SEQ ID NO 31
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 31
cagagctata cggag                                                         15

<210> SEQ ID NO 32
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 32
gctactctgg gtgct                                                         15

<210> SEQ ID NO 33
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 33
tgtccactgt caggg                                                         15

<210> SEQ ID NO 34
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 34
ataatagagg acgga                                                         15

<210> SEQ ID NO 35
```

```
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 35
tgagctcttc caggt                                                     15

<210> SEQ ID NO 36
<211> LENGTH: 58
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 36
tgaagagcgt ggtgcagtcg ttctcttcag cgatggcgaa gcccacccat gttagtga     58

<210> SEQ ID NO 37
<211> LENGTH: 15
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 37
gagaaggata tcact                                                     15

<210> SEQ ID NO 38
<211> LENGTH: 8
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 38 atatcact                                                              8

<210> SEQ ID NO 39
<211> LENGTH: 83
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 39
ctgaagagcg tggtgcagtc gttctcttca gcgatgacgt cagtccaccc atgttagtga   60
tgcatggaga gcgattcact aac                                           83

<210> SEQ ID NO 40
<211> LENGTH: 98
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 40
ctgaagagcg tggtgcagtc gttctcttca gcgatgacgt acacgtagca tctgacagtc   60
cacccatgtt agtgatgcat ggagagcgat tcactaac                           98

<210> SEQ ID NO 41
<211> LENGTH: 48
<212> TYPE: DNA
<213> ORGANISM: ARTIFICIAL SEQUENCE
<220> FEATURE:
```

```
<223> OTHER INFORMATION: CHEMICALLY SYNTHESIZED SEQUENCE

<400> SEQUENCE: 41
ggaagatcga cccaaagtac gcagatcttc cgagccggtc gaagttac                48

<210> SEQ ID NO 42
<211> LENGTH: 54
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 42
ggaagatcat gacccaaagt acgcaatgat cttccgagcc ggtcgaagtt acta          54

<210> SEQ ID NO 43
<211> LENGTH: 17
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 43
tactagagat caatgat                                                   17

<210> SEQ ID NO 44
<211> LENGTH: 9
<212> TYPE: DNA
<213> ORGANISM: ARTIFICIAL SEQUENCE
<220> FEATURE:
<223> OTHER INFORMATION: CHEMICALLY SYNTHESIZED SEQUENCE

<400> SEQUENCE: 44 atcaatgat                                                             9
```

MEDIUM SCALE INTEGRATION OF MOLECULAR LOGIC GATES IN AN AUTOMATON

This application is a continuation of U.S. Ser. No. 11/904,667, filed Sep. 28, 2007, which claims the benefit of U.S. Provisional Application No. 60/847,873, filed Sep. 28, 2006, the contents of each of which are hereby incorporated by reference into this application.

The invention disclosed herein was made with Government support under National Science Foundation grants IIS-0324845, CCF-0523317, and CHE-0533065 and NSF CAREER Grant 0238027. Accordingly, the U.S. Government has certain rights in this invention.

Throughout this application, various publications are referenced in parentheses by number. Full citations for these references may be found at the end of each experimental section. The disclosures of these publications in their entireties are hereby incorporated by reference into this application to more fully describe the state of the art to which this invention pertains.

BACKGROUND OF THE INVENTION

Molecular computation and circuits engineering (1-27) using a "silicomimetic" approach is currently focused on building molecular networks analogous to electrical engineering designs. These networks consist of logic gates, which perform Boolean logical operations such as AND, NOT, and OR on one or more inputs to produce an output. While individual molecular gates and small networks have previously been constructed, these gates are yet to be integrated at higher levels of complexity. Such integration in electrical engineering arises from massive parallelism and interconnections, rather than fundamental component complexity. The ability to truly integrate molecular components remains crucial for the construction of next-generation molecular devices (11, 14).

The largest solution-phase molecular circuits previously considered include networks combining up to 20 logic modules (11-20). On a similar scale, utilizing a full set of deoxyribozyme-based logic gates (6, 19, 24), solution-phase computing circuits have been constructed such as a half-adder (7), ligase-phosphodiesterase cascades (19), and most recently a full-adder that comprises 7 logic gates in a single tube (24).

SUMMARY OF THE INVENTION

A composition is provided comprising:
(i) (a) a first plurality of deoxyribozymes, each deoxyribozyme of which cleaves a first substrate when contacted with a first oligonucleotide of a plurality of oligonucleotides but not when contacted with any one of the remainder of the plurality of oligonucleotides;
(b) a second plurality of deoxyribozymes, each deoxyribozyme of which cleaves the first substrate when contacted with a second and a third oligonucleotide of the plurality of oligonucleotides;
(c) a third plurality of deoxyribozymes, each deoxyribozyme of which cleaves the first substrate when contacted with a fourth and a fifth oligonucleotide of the plurality of oligonucleotides and in the absence of a sixth oligonucleotide of the plurality of oligonucleotides; and
(ii) a fourth plurality of deoxyribozymes, each deoxyribozyme of which cleaves a second substrate when contacted with a first oligonucleotide of a plurality of oligonucleotides a first substrate and a second substrate, wherein the first substrate comprises a first fluorophore and the second substrate comprises a second fluorophore, and wherein cleavage of the first substrate causes an increase in fluorescence of the first fluorophore and cleavage of the second substrate causes an increase in fluorescence of the second fluorophore, and wherein the first and second fluorophores have different emission spectra, and wherein the first, second, third and fourth pluralities of deoxyribozymes are distributed in a plurality of compartments such that each compartment contains (i) the first substrate, (ii) the second substrate, (iii) at least two deoxyribozymes, each of which is, independently, of the first, second, third or fourth plurality of deoxyribozymes.

A method is provided of optically detecting the presence of a plurality of oligonucleotides in a sample, wherein each oligonucleotide to be detected comprises consecutive nucleotides having a sequence different than the remaining oligonucleotides of the plurality, comprising:
(a) adding a portion of the sample to each of a plurality of compartments, wherein each compartment comprises (i) a first substrate, (ii) a second substrate, (iii) at least one deoxyribozyme of a first or a second plurality of deoxyribozymes, (iii) at least one deoxyribozyme of a third plurality of deoxyribozymes, and (iv) at least one deoxyribozyme of a fourth plurality of deoxyribozymes and wherein (a) each deoxyribozyme of the first plurality of deoxyribozymes cleaves the first substrate when contacted with a first oligonucleotide of a plurality of oligonucleotides but not when contacted with any one of the remainder of the plurality of oligonucleotides; (b) each deoxyribozyme of the second plurality of deoxyribozymes cleaves the first substrate when contacted with a second and a third oligonucleotide of the plurality of oligonucleotides; (c) each deoxyribozyme of the third plurality of deoxyribozymes cleaves the first substrate when contacted with a fourth and a fifth oligonucleotide of the plurality of oligonucleotides and in the absence of a sixth oligonucleotide of the plurality of oligonucleotides; and (d) each deoxyribozyme of the fourth plurality of deoxyribozymes cleaves the second substrate when contacted with a first oligonucleotide of a plurality of oligonucleotides, and wherein the first substrate comprises a first fluorophore and the second substrate comprises a second fluorophore, and wherein cleavage of the first substrate causes an increase in fluorescence of the first fluorophore and cleavage of the second substrate causes an increase in fluorescence of the second fluorophore, and wherein the deoxyribozymes are distributed among the compartments such that the presence of one oligonucleotide or the presence of two different oligonucleotides of the plurality in causes an increase in fluorescence of the first or second fluorophore in a compartment of the plurality;
(b) quantifying the fluorescence of each of the first fluorophore and of the second fluorophore in each of the plurality of compartments; and
(c) determining from the fluorescence of each of first fluorophore and of the second fluorophore quantified in step (b) the presence or absence of one or more of the plurality of oligonucleotides in each of the eight compartments, thereby detecting the presence of the presence of the plurality of oligonucleotides in the sample.

DETAILED DESCRIPTION OF THE INVENTION

Figure 1:
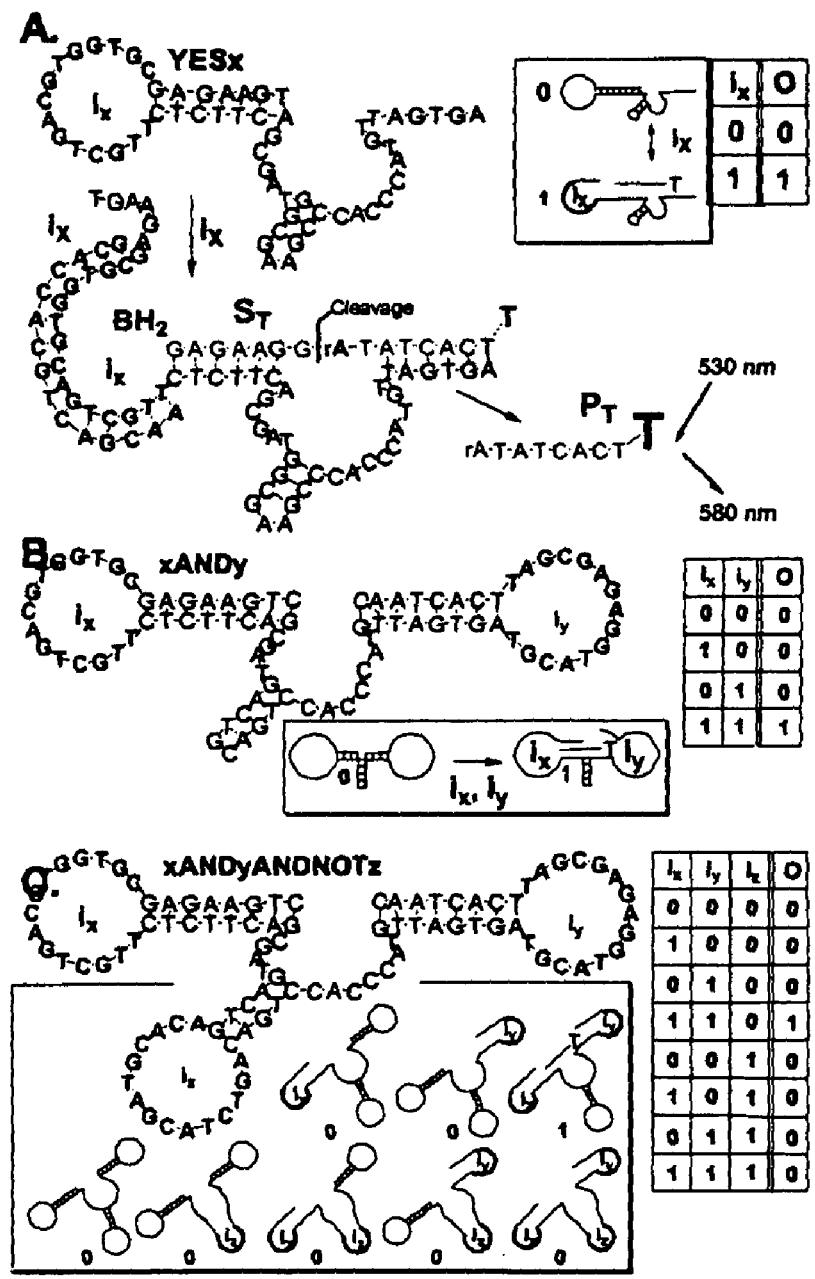
FIG. 1: Automaton move gates and logic gate structures: (A) Automaton move gates were designed from E6 deoxyribozyme-based logic gates (SEQ ID NO:36) (7, 24, 33). Upon addition of activating input (SEQ ID NO:1), these gates cleave substrate $S_T$ (SEQ ID NO:37) to produce $P_T$ (SEQ ID NO:38) and an increase in TAMRA (T) fluorescence. YESx gates are activated by a single input x. (B) xANDy gates (SEQ ID NO:39) are activated in the presence of two inputs x and y. (C) xANDyANDNOTz gates (SEQ ID NO:40) are activated in the presence of inputs x and y only if a third inhibiting input "z" is not present. Inserts show a truth table of logic gate behavior.

A composition is provided comprising:
(i) (a) a first plurality of deoxyribozymes, each deoxyribozyme of which cleaves a first substrate when contacted with a first oligonucleotide of a plurality of oligonucleotides but not when contacted with any one of the remainder of the plurality of oligonucleotides;
  (b) a second plurality of deoxyribozymes, each deoxyribozyme of which cleaves the first substrate when contacted with a second and a third oligonucleotide of the plurality of oligonucleotides;
  (c) a third plurality of deoxyribozymes, each deoxyribozyme of which cleaves the first substrate when contacted with a fourth and a fifth oligonucleotide of the plurality of oligonucleotides and in the absence of a sixth oligonucleotide of the plurality of oligonucleotides; and
  (ii) a fourth plurality of deoxyribozymes, each deoxyribozyme of which cleaves a second substrate when contacted with a first oligonucleotide of a plurality of oligonucleotides a first substrate and a second substrate,
wherein the first substrate comprises a first fluorophore and the second substrate comprises a second fluorophore, and wherein cleavage of the first substrate causes an increase in fluorescence of the first fluorophore and cleavage of the second substrate causes an increase in fluorescence of the second fluorophore, and wherein the first and second fluorophores have different emission spectra, and wherein the first, second, third and fourth pluralities of deoxyribozymes are distributed in a plurality of compartments such that each compartment contains (i) the first substrate, (ii) the second substrate, (iii) at least two deoxyribozymes, each of which is, independently, of the first, second, third or fourth plurality of deoxyribozymes.

In an embodiment, each compartment contains (i) at least one deoxyribozyme of the first or second plurality of deoxyribozymes, (ii) at least one deoxyribozyme of the third plurality of deoxyribozymes, and (iii) at least one deoxyribozyme of the fourth plurality of deoxyribozymes.

In an embodiment, the deoxyribozyme comprises consecutive nucleotides having a sequence identical to, or complementary to, any of SEQ ID NOs. 1-32.

In an embodiment, in (i) (a), for each deoxyribozyme of the plurality of the deoxyribozymes, the first oligonucleotide comprises consecutive nucleotides having a sequence different than the sequence of each of the remainder of the plurality of oligonucleotides.

In an embodiment, in (i) (b), for each deoxyribozyme of the second plurality of the deoxyribozymes, the second and third oligonucleotides each comprise consecutive nucleotides each having a sequence different than the sequence of each other, and different than the sequence of each of the remainder of the plurality of oligonucleotides.

In an embodiment, the second or third oligonucleotide of (i)(b) have a sequence identical to the sequence of the first oligonucleotide of (i)(a).

In an embodiment, in (i) (c), for each deoxyribozyme of the third plurality of the deoxyribozymes, the fourth, fifth and sixth oligonucleotides each comprise consecutive nucleotides each having a sequence different than the sequence of each other, and different than the sequence of each of the remainder of the plurality of oligonucleotides.

In an embodiment, the fourth, fifth or sixth oligonucleotides of (i)(c) have a sequence identical to the sequence of the first oligonucleotide of (i)(a).

In an embodiment, the composition comprises eight compartments or sixteen compartments. In an embodiment, each compartment contains up to 20 deoxyribozymes.

A method is provided of optically detecting the presence of a plurality of oligonucleotides in a sample, wherein each oligonucleotide to be detected comprises consecutive nucleotides having a sequence different than the remaining oligonucleotides of the plurality, comprising:
(d) adding a portion of the sample to each of a plurality of compartments, wherein each compartment comprises (i) a first substrate, (ii) a second substrate, (iii) at least one deoxyribozyme of a first or a second plurality of deoxyribozymes, (iii) at least one deoxyribozyme of a third plurality of deoxyribozymes, and (iv) at least one deoxyribozyme of a fourth plurality of deoxyribozymes and wherein (a) each deoxyribozyme of the first plurality of deoxyribozymes cleaves the first substrate when contacted with a first oligonucleotide of a plurality of oligonucleotides but not when contacted with any one of the remainder of the plurality of oligonucleotides; (b) each deoxyribozyme of the second plurality of deoxyribozymes cleaves the first substrate when contacted with a second and a third oligonucleotide of the plurality of oligonucleotides; (c) each deoxyribozyme of the third plurality of deoxyribozymes cleaves the first substrate when contacted with a fourth and a fifth oligonucleotide of the plurality of oligonucleotides and in the absence of a sixth oligonucleotide of the plurality of oligonucleotides; and (d) each deoxyribozyme of the fourth plurality of deoxyribozymes cleaves the second substrate when contacted with a first oligonucleotide of a plurality of oligonucleotides, and wherein the first substrate comprises a first fluorophore and the second substrate comprises a second fluorophore, and wherein cleavage of the first substrate causes an increase in fluorescence of the first fluorophore and cleavage of the second substrate causes an increase in fluorescence of the second fluorophore, and wherein the deoxyribozymes are distributed among the compartments such that the presence of one oligonucleotide or the presence of two different oligonucleotides of the plurality in causes an increase in fluorescence of the first or second fluorophore in a compartment of the plurality;

(e) quantifying the fluorescence of each of the first fluorophore and of the second fluorophore in each of the plurality of compartments; and (f) determining from the fluorescence of each of first fluorophore and of the second fluorophore quantified in step (b) the presence or absence of one or more of the plurality of oligonucleotides in each of the eight compartments, thereby detecting the presence of the presence of the plurality of oligonucleotides in the sample.

In an embodiment, up to sixteen oligonucleotides are detected and the plurality of compartments consists of eight compartments.

In an embodiment, up to thirty two oligonucleotides are detected and the plurality of compartments consists of sixteen compartments.

In an embodiment, the deoxyribozyme comprises consecutive nucleotides having a sequence identical to, or complementary to, any of SEQ ID NOs. 1-32.

In an embodiment, one or more of the plurality of oligonucleotides has the sequence of a portion of a nucleic acid from a pathogenic organism.

In an embodiment, in (i)(a), for each deoxyribozyme of the plurality of the deoxyribozymes, the first oligonucleotide comprises consecutive nucleotides having a sequence different than the sequence of each of the remainder of the plurality of oligonucleotides.

In an embodiment, in (i)(b), for each deoxyribozyme of the second plurality of the deoxyribozymes, the second and third oligonucleotides each comprise consecutive nucleotides each having a sequence different than the sequence of each other, and different than the sequence of each of the remainder of the plurality of oligonucleotides.

In an embodiment, the second or third oligonucleotide of (i)(b) have a sequence identical to the sequence of the first oligonucleotide of (i)(a).

In an embodiment, in (i)(c), for each deoxyribozyme of the third plurality of the deoxyribozymes, the fourth, fifth and sixth oligonucleotides each comprise consecutive nucleotides each having a sequence different than the sequence of each other, and different than the sequence of each of the remainder of the plurality of oligonucleotides.

In an embodiment, the fourth, fifth or sixth oligonucleotides of (i)(c) have a sequence identical to the sequence of the first oligonucleotide of (i)(a).

Experimental Results

The largest solution-phase molecular circuits previously considered include networks combining up to 20 logic modules (11-20). On a similar scale, utilizing a full set of deoxyribozyme-based logic gates (6, 19, 24), solution-phase computing circuits have been constructed such as a half-adder (7), ligase-phosphodiesterase cascades (19), and most recently a full-adder that comprises 7 logic gates in a single tube (24).

Systems of greater complexity include molecular automata (4, 8-10), which are capable of analyzing a series of human or environmental inputs in a meaningful fashion. An unbiased test of automaton construction is game playing, and tic-tac-toe, one of the simplest games of perfect information and yet a surprisingly complex combinatorial problem, with $2.65 \times 10^{103}$ nonlosing strategies for a complete version of tic-tac-toe (28), is used herein to demonstrate the efficacy of the disclosed automatons. A deoxyribozyme-based molecular automaton (MAYA-I, a molecular array of YES and AND gates) that plays a simplified symmetry-pruned game of tic-tac-toe encompassing 19 permissible game plays, using an array of 23 logic gates distributed over 8 wells (8) has previously been published.

Here, the development of the first solution-phase molecular assembly comprising over 100 molecular logic gates, which more than quadruples the complexity performed by any previous system. "MAYA-II" is a second generation molecular automaton capable of playing a complete game of tic-tac-toe against a human opponent, and encompasses 76 permissible game plays. MAYA-II is more user-friendly than MAYA-I, as it signals both players move in a two-color output system and imposes no constraints on the position of the human player's first move. MAYA-II is constructed from three classes of stem-loop controlled deoxyribozyme-based logic gates that are allosterically modulated by input oligonucleotides to produce fluorescent output signals (FIG. 1) (6-8): (i) YESx gates are activated by a single input x; (ii) xANDy gates are activated in the presence of two inputs x and y; and (iii) xANDyAND-NOTz gates are activated in the presence of inputs x and y only if a third inhibiting input z is absent. To play MAYA-II, a set of deoxyribozyme-based logic gates are arranged according to a predetermined strategy in a 3×3 array within a 384-well assay plate (see FIG. 2A). Oligonucleotide inputs encoding the human moves are added successively to the wells and trigger the automaton's next move. After each input addition, the well-plate is analyzed using a fluorescent plate reader which follows accumulation of two fluorescent oligonucleotide outputs display of the human move is observed in the "green" fluorescein output channel, and the automaton's response to the human input addition is observed in the "red" tetramethylrhodamine (TAMRA) output channel. An example game is shown in FIG. 2B.

The game strategy for MAYA-II (FIG. 2A) is considerably different from MAYA-I. The automaton still moves first into the middle square (well 5) controlled by a constitutively active deoxyribozyme added immediately prior to the beginning of the game. However successive automaton moves are constructed as a hierarchical cascade of AND gates, with YES gates responding to the first human move (NOT loops are included to prevent secondary activation in already played wells or are redundant and included to minimize cumulative nondigital behavior in side wells over several moves). In doing this, MAYA-II is a step toward programmable and generalizable MAYAs that are trainable to play any game strategy. The strategy employed herein required 32 input oligonucleotides, encoding both the position and timing of a human move. These inputs are named 1 nm wherein N is the position of the move (wells 1-4 or 6-9), and M is the timing of the move (1 for the first move, 2 for the second move, etc.). For example, input 162 would be added to every well when a human would like to indicate to the automaton they are moving into square 6 as their second move. This strategy was translated into Boolean logic amenable to deoxyribozyme-based implementation (FIG. 2) using a custom computer program, resulting in 96 logic gates for automaton move calculations and an additional 32 logic gates to display human moves. Considering traditional difficulties in selecting nucleic acids suitable for computation (29, 30) and the relatively high concentration of individual gates needed to accomplish readable outputs, it was far from certain at the outset of this project that such a number of inputs and gates could be coordinated in solution.

The 32 input oligonucleotide sequences (Table 1) were chosen to investigate both the inherent generality of the logic gate design, and the ability to derive inputs using computer assistance (akin to previous system designs (31)). In contrast to MAYA-I, where a smaller number of inputs meant trial-and-error substitution of inputs was feasible, an algorithm was used specifically devised for this purpose (i) A theoretical library of stem-loop structures (containing a stem of 5 base-pairs and a loop of 15 nucleotides) was generated by applying a search algorithm, based on simple combinatorial constants (32) where loops containing stronger internal structures of more than two base-pairs were eliminated, (ii) of the 10,795 generated sequences, a set of 32 15-mer loop sequences with no more than four nucleotides in common in a continuous stretch were selected for trial as oligonucleotide inputs and randomly assigned to human move and order positions, (iii) these sequences were inserted into deoxyribozyme gate structures and analyzed using mfold (32) (iv) input sequences inducing gate misfolding were discarded and replaced with the next inputs from our library, (v) canonical gates and their reverse complement 15-mer input sequences were custom-synthesized and tested in solution-phase for digital gate behavior, (vi) inputs and gates failing to show expected digital behavior were substituted with the next input from our collection. Tested input sequences are listed in Table 1. Out of the initial set of 32 inputs only three were rejected and substituted. Thus, while there is still space for improvement in the design of the algorithm, it led to minimization of trial-and-error from the input selection.

Figure 2:
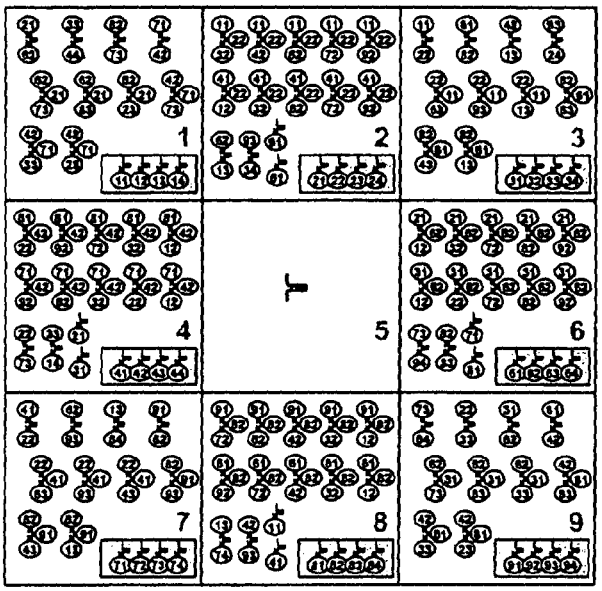
FIG. 2: (A) Schematic representation of MAYA-II. One-, two-, and three-input deoxyribozyme-based logic gates are allosterically modulated by 32 human-operated input oligonucleotides. 96 logic gates and one constitutively active deoxyribozyme distributed across nine wells calculate automaton moves, and 32 gates (boxed) display human moves by implementation of a two-color fluorogenic output system. (B) A representative game Gates and active deoxyribozyme were mixed with 0.5 μM $S_F$, 1 μM $S_T$ and dispensed into nine wells of a 384-well plate. Inputs (1 μM) were added in sequence into each well to signal the human players move, and both fluorescein (F) and TAMRA (T) fluorescence was measured every 15 min for 60 min in between each move. Results are expressed as the slope of signal increase over time (dFmin (−1)).
Figure 2:
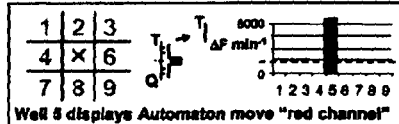
Figure 2:
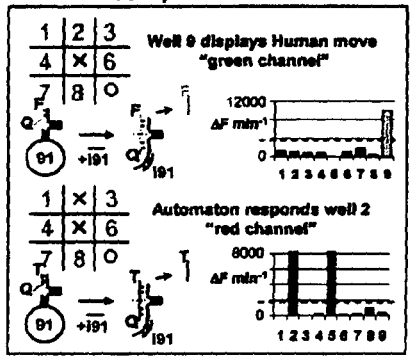
Figure 2:
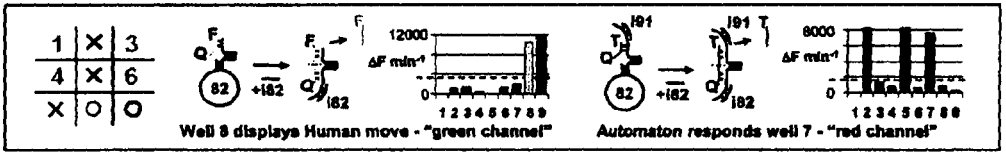
Figure 2:
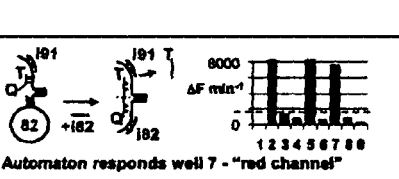
Figure 2:
Figure 2:
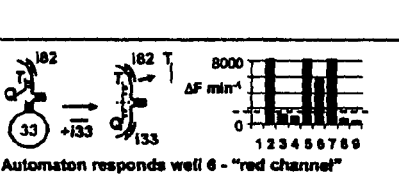
Figure 2:
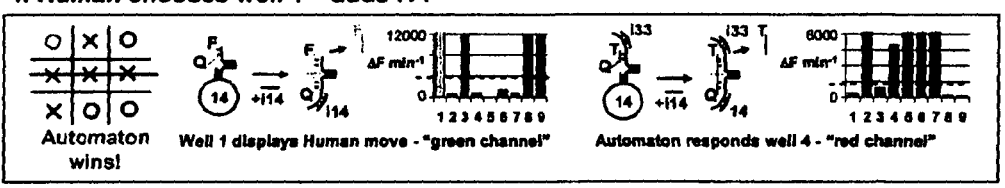
Figure 2:
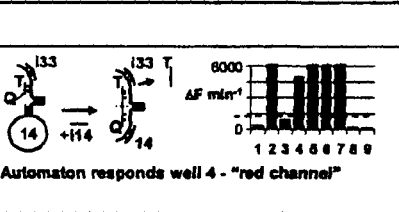
Figure 3:
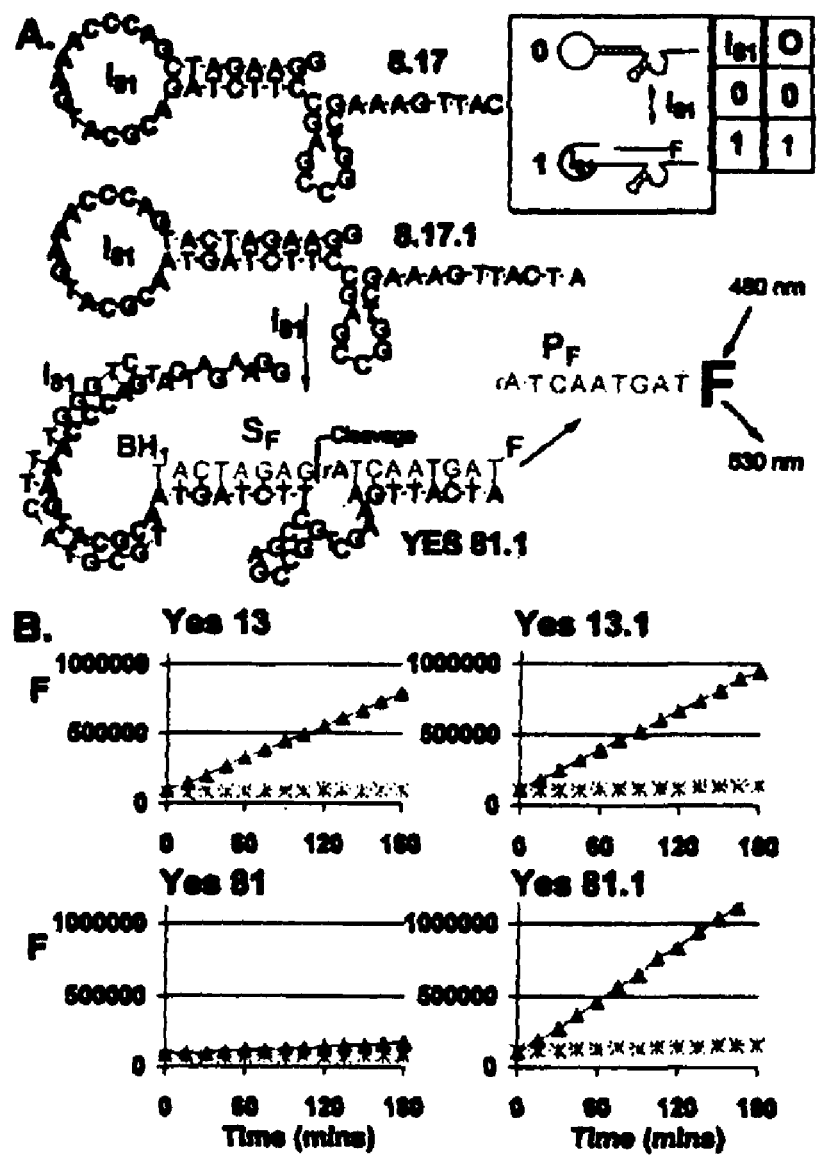
FIG. 3: Human move gates: (A) Human move gates were designed from 8.17 deoxyribozyme-based logic gates (7, 24-54) (SEQ ID NO:41). Upon addition of activating input (SEQ ID NO:25), these gates cleave substrate $S_T$ (SEQ ID NO:43) to produce product $P_F$ (SEQ ID NO:44) and an increase in fluorescein fluorescence (F). Lengthening of the substrate binding region created 8.17.1 (SEQ ID NO:42), with more reliable enzyme activity. The insert shows a truth table of logic gate behavior. (B) Raw fluorescence activity (F) of 8.17 and 8.17.1-based gates (20 μM) using 1 μM ST in the presence (triangles) or absence (stars) of 1 μM inputs. Gates derived from 8.17 were variably active, as demonstrated here by Yes 13 (active) and Yes 81 (not active), whereas gates derived from 8.17.1 were always active, as displayed for Yes 13.1 and Yes 81.1.

All automaton response gates were constructed from deoxyribozyme E6 (7, 24, 33) (FIG. 1), which cleaves oligonucleotide substrate $S_T$ to produce product $P_T$ and an increase in "red channel" TAMRA (T) fluorescence. Variable signal intensity was detected in some gates, and signal optimization was achieved by manipulating the 5' or 3' ends of the gate molecule, reversing the input loop sequences, or removing redundant NOT loops (summarized in Table 1). For human move visualization 8-17-based deoxyribozyme logic gates were used (7, 24, 34) which cleave substrate $S_F$ to produce product $P_F$ and an increase in "green channel" fluorescein (F) fluorescence. However, only two input sequences were found to be active, and the underlying enzyme was re-engineered by lengthening the substrate binding region (FIG. 3A) leading to the perfect digital behavior of all inputs (FIG. 3B). After individual testing and optimization, gates were mixed according to the MAYA-II algorithm (FIG. 2) and retested for digital behavior to exclude the possibility of undesirable cross reactivity. Results were expressed as the slope of fluorescence change over time ($\Delta F$ min $(-1)$, FIG. 2). Automaton move gates with slopes greater than 3000 $\Delta F$ min $(-1)$ were considered positive, and signals smaller than 2000 $\delta F$min $(-1)$ were discounted as background noise Human move gates tended to give higher signals and rates of reaction over time and were thus included at lower concentrations. Even so, these gates typically gave a positive reaction of greater than 5000 $\Delta F$ min $(-1)$, and reactions smaller than 4000 $\Delta F$ min $(-1)$ were considered noise. While most gates were not adversely affected within the mixtures, variable signal intensity was observed for some automaton move gates, and these were optimized either as described above, or by altering the concentration of individual gates within the mix. Interestingly, a directly proportional signal to concentration ratio was not observed for every gate, as some gates were inhibited by increasing concentrations within the mix.

TABLE 1

Input Sequences for MAYA-II and Modifications Required for Human Move Gates.

| | | | 5'AND | | | 3'AND | | | | |
| | | | | Modified | | | Modified | | | |
| inputs and sequence[a] | YES/M | total | + | − | R | total | + | − | R | NOT/x |
|---|---|---|---|---|---|---|---|---|---|---|
| I11 AACGACTGCACCACG | 1 | 6 | | | | | | | | 3/x3 |
| I12 CTCTCCCTGTACCCA | | 2 | | 2 | 5 | | | | | |
| I13 ACCCCTCTCGCTCTT | | 1 | | | | 6 | | −4 | 1 | |
| I14 TTCTGCCTTGATCCG | | | | | | 1 | | | | |
| I21 TGTTGTCTTATCCAT | 1 | 5 | | −4 | | 1 | | | 1 | 3 |
| I22 TCAGATGCTACGTGT | | 6 | | | | 7 | | | 2 | 10 |
| I23 ACCGTACTCGACCTA | | | | | | 3 | | −1 | | |
| I24 TCGGATCTCGGTTTC | | | | | | 1 | | −1 | | |
| I31 TACACGCTGGTCAAT | 1 | 5 | | −4 | | 1 | | | 1 | 3 |
| I32 CACTATCTCGAATCA | | | | | | 7 | +5 | | | |

TABLE 1-continued

Input Sequences for MAYA-II and Modifications Required for Human Move Gates.

| inputs and sequence[a] | YES/M | 5'AND total | Modified + | − | R | 3'AND total | Modified + | − | R | NOT/x |
|---|---|---|---|---|---|---|---|---|---|---|
| I33 | GCGTGACTGCGGCAT | | 1 | | | | 6 | | −1 | 1 | |
| I34 | GTTGGTCTTGTAGGA | | | | | | 1 | | | | |
| I41 | GCTAGGCTATCGCGT | 1/1 | 6 | | | | | | | | 3 |
| I42 | TAATACCTGAGCGGG | | 7 | | −2 | | 6 | +2 | | | 10 |
| I43 | TACCCCCTAGTCTGC | | 1 | | −1 | 1 | 2 | | −1 | | |
| I44 | AACGGACTTCAACAG | | 1 | | −1 | 1 | | | | | |
| I61 | CGGGATCTCGTCGGT | 1 | 6 | +2 | | | | | | | 3 |
| I62 | ATCGCTCTCCATGCA | | 8 | | −4 | | 5 | | | | 10/x10 |
| I63 | ATCTATCTCGTTCCG | | 2 | | | 2 | 1 | | −1 | | |
| I64 | ACTCCGCTCGACTTA | | | | | | 1 | | | | |
| I71 | GGATCACTTACGTAT | 1/+1 | 6 | +1 | | | | | | | 3 |
| I72 | GGTAGCCTTTTATCG | | | | | | 7 | +4 | | | |
| I73 | CATTGCCTCGATATC | | 2 | | | | 5 | | −1 | | |
| I74 | CCAGACCTTTCAAGT | | | | | | 1 | | | | |
| I81 | TGCGTACTTTGGGTC | 1 | 6 | | | | | | | | 3 |
| I82 | TCAGGGCTACGCAAG | | 7 | | −6 | | 6 | +1 | −3 | 1 | 10 |
| I83 | TAATTACTGTTTCAC | | 1 | | | | 2 | +2 | | | |
| I84 | GGATGCCTGGCGTCT | | 1 | | −1 | 1 | | | | | |
| I91 | TGCTATCTCGACAAG | 1 | 6 | +1 | | | | | | | 3 |
| I92 | CTCAGGCTGTGTATT | | | | | | 7 | +4 | | | |
| I93 | CAGAGCTATACGGAG | | 2 | | | | 5 | | −1 | | |
| I94 | GCTACTCTGGGTGCT | | | | | | 1 | | | | |
| Totals | | 8/+1/−1 | 88 | +4 | −23 | 7 | 88 | +18 | −14 | 7 | 64/x13 |

From top to bottom—SEQ ID NOs:1-32, respectively.
[a] Inputs rejected: r11, TGTCCACTGTCAGGG (SEQ ID NO:33); r22, ATAATAGAGGACGGA (SEQ ID NO:34); r93 TGAGCTCTTCCAGGT (SEQ ID NO:35). Key YES number of Human move YES gates modified; 5' AND number of 5' AND loops modified; 3' AND, number of 3' AND loops modified; NOT number of NOT loops modified; Modified (M), Number of modified human move gate loops; +, Number of loops with 5' and 3' terminal nucleotides added; −, number of loops with 5' and 3' terminal nucleotides removed; R number with 5' and 3' loops reversed; x number with NOT loop removed.

Upon establishment of the final conditions, MAYA-II was constructed as a set of eight tubes (the Well 5 tube containing active deoxyribozyme was sometimes omitted), and all 76 tic-tac-toe games were repeatedly tested. MAYA-II was able to play perfectly a general tic-tac-toe game by successfully signaling both human and automaton moves. Small immediate increases of fluorescence upon input addition, most likely the result of a conformational change of a gate complexed with substrate, were occasionally observed at the first measurement (the first 15 min of reaction), however this was distinguishable from positive signals as the fluorescence did not continue to increase. Thus, digital behavior could be reliably confirmed within 30 min of input addition. An example game is shown in FIG. 2, and the results from all 76 games are provided in the Supporting Information.

The success of MAYA-II indicates the maturity of this deoxyribozyme-based logic gate system as a "plug and play" integrated logic gate system. MAYA-II integrates 128 molecular logic gates, 32 oligonucleotide inputs, and 8 two-channel fluorescent outputs across 8 wells. It could be argued that by integrating more than 100 molecular logic gates in a single system, MAYA-II represents the first "medium-scale integrated molecular circuit" in solution. This increased complexity of MAYA-II has enabled refinement of a deoxyribozyme logic gate model, allowing the development of design principles for optimizing digital gate behavior15 and the generation of a library of known input sequences (Table 1). The symmetrical game strategy enabled the entire game to be essentially encoded as a series of YES and AND gates, which take into account only two human moves: the current and preceding. A total of 152 gates could be used to encode any symmetrical game strategy into any automaton using the above-defined 32 inputs and allowing for subsequent additional activation in already played wells.

This massive parallel integration can be used, inter alia, in oligonucleotide analysis. For example, the ability to detect and analyze combinations of multiple DNA sequences within minutes has direct applications in microarray style diagnostics. Automata the size of MAYA-II analyze the space of $2^{32}$ possible subsets of the 32 input oligonucleotides and partition it into equivalence classes signaled by unique two-color, eight-well patterns, for a total of up to $2^{16}$=65,536 patterns. Based on MAYA-II, we are currently developing several systems for multiplex SNP detection and viral lineage attribution. Moreover, the versatility of the input and output system allows coupling of logic gate processing to both upstream and downstream events, such as the detection and release of small molecules and the inhibition of enzymatic activity (37).

REFERENCES (1) Adleman, L. M. Science 1994, 266, 1021-4.
(2) Elowitz, M. B.; Leibler, S. Nature 2000. 403, 335-8.
(3) Mao, C; LaBcan, T. H.; Relf, J. H.; Seeman, N. C. Nature 2000, 407. 493-6.
(4) Benenson. Y.; Paz-Elizur, T.; Adar, R.; Keinan, E.; Livnch, Z.; Shapiro, E. Nature 2001. 414, 430-4.
(5) Braich, R. S.; Chelyapov, N.; Johnson, C; Rothemund, P. W.; Adleman, L. Science 2002, 296, 499-502.
(6) Stojanovic, M. N.; Mitchell, T. E.; Stefanovic, D. J. Am. Chem. Soc. 2002, 124. 3555-61.
(7) Stojanovic, M. N.; Stefanovic, D. J. Am. Chem. Soc. 2003, 125, 6673-6.
(8) Stojanovic, M. N.; Stefanovic, D. Nat. Biotechnol. 2003, 21, 1069-74.
(9) Adar, R.; Benenson, Y.; Linshiz, G.; Rosner, A.; Tishby, N.; Shapiro, E. Proc. Natl. Acad. Sci. U.S.A. 2004, 101, 9960-5.
(10) Benenson, Y.; Gil, B.; Ben-Dor, U.; Adar, R.; Shapiro, E. Nature 2004, 429, 423-9.
(11) de Silva. A. P.; McClenaghan, N. D. Chemistry 2004, 10, 574-86.
(12) Rothemund, P. W.; Papadakis, N.; Winfree, E., PLOS Biol. 2004, 2. c424.
(13) Schmidt, K. A.; Henkel, C. V.; Rozenberg, G.; Spaink. H. P. Nucleic Acids Res. 2004, 32, 4962-8.
(14) Simpson, M. L. Trends Biotechnol. 2004, 22, 555-7.
(15) Su, X.; Smith, L. M. Nucleic Acids Res. 2004, 32, 3115-23.
(16) Szacilowski, K. Chemistry 2004, 10, 2520-8.
(17) Benner, S. A.; Sismour, A. M. Nat. Rev. Genet. 2005, 6. 533-43.
(18) Grover, W H, Mathies, R A. Lab Chip 2005, 5:1031-40
(19) Stojanovic, M N, Semova, S, Kolpashchikov, D, Macdonald, J, Morgan, C, Stefanovic, D, J. Am. Chem. Soc. 2005, 127, 6914-5
(20) de Silva, A P, Leydet, Y, Lmcheneau. C, McClenaghan, N D, J. Phys. Condens. Matter 2006, 18:S1847-72
(21) Henkel, C V, Back, T, Kok, J N, Rozenbcrg, G, Spaink, H P Biosystems, 2006
(22) Isaacs, F J, Dwyer, D J, Collins, J J Nat Biotethnol 2006, 24, 545-54
(23) Komiya. K, Sakamoto, K, Kameda, A, Yamamoto, M, Ohuchi, A, Kiga, D, Yokoyama, S, Hagiya, M, Biosystems 2006. 83:18-25
(24) Lederman, H, Macdonald, J, Stefanovic, D, Stojanovic, M N, Biochemistry 2006, 45, 1194-99
(25) Liu, Y, Jiang, W, Zhang, H Y, Li, C J, J. Phys. Chem. B 2006, 110, 14231-35
(26) Magri, D C, Brown, G J, McClean, G D, de Silva, A P, J. Am. Chem. Soc. 2006, 725, 4950-1
(27) Penchovsky, R, Breaker, R R, Nat. Biotechnol. 2005, 23, 1424-33
(28) Andrews, B, Games, Strategies, and Boolean Formula Manipulation In Dept of Computer Science Uni. of New Mexico UNM CS Tech Rep TR-CS-2005-41, University of New Mexico N. Mex., 2005
(29) Mauri, G, Ferretti, C, In Word design for molecular computing: A survey, 9th International Workshop on DNA-Based Computers, 2003, Springer, 2004. pp 37-46
(30) Sager, J, Stefanovic, D, In Designing Nucleotide Sequences for Computation: A Survey of Constraints, 11th International Workshop on DNA-Based Computers, 2005, Springer, 2006, pp 275-289
(31) Seeman, N C, J. Theor. Biol. 1982, 99:237-47
(32) Zuker, M, Nucleic Acids Res. 2003, 31, 3406-15
(33) Breaker. R R, Joyce, G F, Chem. Biol. 1995, 2, 655-60
(34) Santoro. S W, Joyce, G F, Proc. Natl. Acad. Sci. USA 1997, 94:4262-6
(35) Macdonald, J, Stefanovic, D, Stojanovic, M N, Solution-Phase Molecular-Scale Computation With Deoxyribozyme-Based Logic Gates and Fluorescent Readouts In Fluorescent energy transfer nucleic acid probes designs and protocols, Didenko, V V, Ed., Humana Press Inc Totowa, N.J., 2006, Vol 335, pp 343-363
(36) Wright. M C, Joyce, G F Science 1997, 276, 614-617
(37) Kolpashchikov, D M, Stojanovic, M N, J. Am. Chem. Soc. 2005, 127, 11348-51

What is claimed is:

1. A composition comprising:
   (i) (a) a first plurality of deoxyribozymes, each deoxyribozyme of which cleaves a first substrate when contacted with a first oligonucleotide of a plurality of oligonucleotides but not when contacted with any one of the remainder of the plurality of oligonucleotides;
   (b) a second plurality of deoxyribozymes, each deoxyribozyme of which cleaves the first substrate when contacted with a second and a third oligonucleotide of the plurality of oligonucleotides;
   (c) a third plurality of deoxyribozymes, each deoxyribozyme of which cleaves the first substrate when contacted with a fourth and a fifth oligonucleotide of the plurality of oligonucleotides and in the absence of a sixth oligonucleotide of the plurality of oligonucleotides; and
   (ii) a fourth plurality of deoxyribozymes, each deoxyribozyme of which cleaves a second substrate when contacted with a first oligonucleotide of a plurality of oligonucleotides,
   wherein the first substrate comprises a first fluorophore and the second substrate comprises a second fluorophore, and wherein cleavage of the first substrate causes an increase in fluorescence of the first fluorophore and cleavage of the second substrate causes an increase in fluorescence of the second fluorophore, and wherein the first and second fluorophores have different emission spectra, and wherein the first, second, third and fourth pluralities of deoxyribozymes are distributed in a plurality of compartments such that each compartment contains (i) the first substrate, (ii) the second substrate, (iii) at least two deoxyribozymes, each of which is, independently, of the first, second, third or fourth plurality of deoxyribozymes.

2. The composition of claim 1, wherein each compartment contains (i) at least one deoxyribozyme of the first or second plurality of deoxyribozymes, (ii) at least one deoxyribozyme of the third plurality of deoxyribozymes, and (iii) at least one deoxyribozyme of the fourth plurality of deoxyribozymes.

3. The composition of claim 1, wherein the deoxyribozyme comprises consecutive nucleotides having a sequence identical to, or complementary to, any of SEQ TD NOs. 1-32.

4. The composition of claim 1, wherein in (i)(a), for each deoxyribozyme of the first plurality of the deoxyribozymes, the first oligonucleotide comprises consecutive nucleotides having a sequence different than the sequence of each of the remainder of the plurality of oligonucleotides.

5. The composition of claim 1, wherein in (i)(b), for each deoxyribozyme of the second plurality of the deoxyribozymes, the second and third oligonucleotides each comprise consecutive nucleotides each having a sequence different than the sequence of each other, and different than the sequence of each of the remainder of the plurality of oligonucleotides.

6. The composition of claim 1, wherein the second or third oligonucleotide of (i)(b) have a sequence identical to the sequence of the first oligonucleotide of (i)(a).

7. The composition of claim 1, wherein in (i)(c), for each deoxyribozyme of the third plurality of the deoxyribozymes, the fourth, fifth and sixth oligonucleotides each comprise consecutive nucleotides each having a sequence different than the sequence of each other, and different than the sequence of each of the remainder of the plurality of oligonucleotides.

8. The composition of claim 1, wherein the fourth, fifth or sixth oligonucleotides of (i) (c) have a sequence identical to the sequence of the first oligonucleotide of (i)(a).

9. The composition of claim 1, comprising eight compartments.

10. The composition of claim 1, wherein each compartment contains up to 20 deoxyribozymes.

11. A method of optically detecting the presence of a plurality of oligonucleotides in a sample, wherein each oligonucleotide to be detected comprises consecutive nucleotides having a sequence different than the remaining oligonucleotides of the plurality, comprising:

(i) adding a portion of the sample to each of a plurality of compartments, wherein each compartment comprises (i) a first substrate, (ii) a second substrate, (iii) at least one deoxyribozyme of a first or a second plurality of deoxyribozymes, (iii) at least one deoxyribozyme of a third plurality of deoxyribozymes, and (iv) at least one deoxyribozyme of a fourth plurality of deoxyribozymes and wherein (a) each deoxyribozyme of the first plurality of deoxyribozymes cleaves the first substrate when contacted with a first oligonucleotide of the plurality of oligonucleotides but not when contacted with any one of the remainder of the plurality of oligonucleotides;

(b) each deoxyribozyme of the second plurality of deoxyribozymes cleaves the first substrate when contacted with a second and a third oligonucleotide of the plurality of oligonucleotides;

(c) each deoxyribozyme of the third plurality of deoxyribozymes cleaves the first substrate when contacted with a fourth and a fifth oligonucleotide of the plurality of oligonucleotides and in the absence of a sixth oligonucleotide of the plurality of oligonucleotides; and (d) each deoxyribozyme of the fourth plurality of deoxyribozymes cleaves the second substrate when contacted with a first oligonucleotide of the plurality of oligonucleotides, and wherein the first substrate comprises a first fluorophore and the second substrate comprises a second fluorophore, and wherein cleavage of the first substrate causes an increase in fluorescence of the first fluorophore and cleavage of the second substrate causes an increase in fluorescence of the second fluorophore, and wherein the deoxyribozymes are distributed among the compartments such that the presence of one oligonucleotide or the presence of two different oligonucleotides of the plurality in causes an increase in fluorescence of the first or second fluorophore in a compartment of the plurality;

(ii) quantifying the fluorescence of each of the first fluorophore and of the second fluorophore in each of the plurality of compartments; and (iii) determining from the fluorescence of each of first fluorophore and of the second fluorophore quantified in step (b) the presence or absence of one or more of the plurality of oligonucleotides in each of the plurality of compartments, thereby detecting the presence of the presence of the plurality of oligonucleotides in the sample.

12. The method of claim 11, wherein up to sixteen oligonucleotides are detected and the plurality of compartments consists of eight compartments.

13. The method of claim 11, wherein up to thirty two oligonucleotides are detected and the plurality of compartments consists of sixteen compartments.

14. The method of claim 11, wherein the deoxyribozyme comprises consecutive nucleotides having a sequence identical to, or complementary to, any of SEQ ID NOs. 1-32.

15. The method of claim 11, wherein one or more of the plurality of oligonucleotides has the sequence of a portion of a nucleic acid from a pathogenic organism.

16. The method of claim 11, wherein in (i)(a), for each deoxyribozyme of the first plurality of the deoxyribozymes, the first oligonucleotide comprises consecutive nucleotides having a sequence different than the sequence of each of the remainder of the plurality of oligonucleotides.

17. The method of claim 11, wherein in (i)(b), for each deoxyribozyme of the second plurality of the deoxyribozymes, the second and third oligonucleotides each comprise consecutive nucleotides each having a sequence different than the sequence of each other, and different than the sequence of each of the remainder of the plurality of oligonucleotides.

18. The method of claim 11, wherein the second or third oligonucleotide of (i)(b) have a sequence identical to the sequence of the first oligonucleotide of (i)(a).

19. The method of claim 11, wherein in (i)(c), for each deoxyribozyme of the third plurality of the deoxyribozymes, the fourth, fifth and sixth oligonucleotides each comprise consecutive nucleotides each having a sequence different than the sequence of each other, and different than the sequence of each of the remainder of the plurality of oligonucleotides.

20. The method of claim 11, wherein the fourth, fifth or sixth oligonucleotides of (i)(c) have a sequence identical to the sequence of the first oligonucleotide of (i)(a).

21. The composition of claim 1, comprising sixteen compartments.

* * * * *